(12) United States Patent
Liou et al.

(10) Patent No.: US 9,186,387 B2
(45) Date of Patent: Nov. 17, 2015

(54) METHOD OF TREATING FATTY LIVER DISEASE

(71) Applicant: HAN SHENG BIOTECH CO., LTD., Pingtung County (TW)

(72) Inventors: Shorong Shii Liou, Kaohsiung (TW); I-Min Liu, Kaohsiung (TW); Chia-Ju Chang, Kaohsiung (TW)

(73) Assignee: HAN SHENG BIOTECH CO., LTD., Pingtung County (TW)

( * ) Notice: Subject to any disclaimer, the term of this patent is extended or adjusted under 35 U.S.C. 154(b) by 0 days.

(21) Appl. No.: 14/171,562

(22) Filed: Feb. 3, 2014

(65) Prior Publication Data

US 2014/0147536 A1    May 29, 2014

Related U.S. Application Data

(62) Division of application No. 13/333,168, filed on Dec. 21, 2011, now abandoned.

(51) Int. Cl.
*A61K 36/232* (2006.01)

(52) U.S. Cl.
CPC ............ *A61K 36/232* (2013.01); *A61K 2236/30* (2013.01)

(58) Field of Classification Search
CPC .................................................. A61K 36/232
See application file for complete search history.

(56) References Cited

U.S. PATENT DOCUMENTS

| 6,455,078 B1 | 9/2002 | Wu |
| 6,720,010 B2 | 4/2004 | Iijima et al. |
| 2012/0035274 A1* | 2/2012 | Park ............................. 514/766 |

OTHER PUBLICATIONS

Rukkumani et al. (2004) J. Med. Food 7 (4), 456-461.*
Sun et al. (2006) Natural Product Research, vol. 20, No. 9, 835-841.*
Besse-Patin et al. (2014) International J. Cell Biology vol. 2014, Article ID 519153, 9 pages.*
Dufour et al. (2006) Clinical Gastroenterology and Hepatology, 4: 1537-1543.*
Mehta et al. (2002) Nutrition Reviews, vol. 60, No. 9, 289-293.*
Adams et al. (2006) Postgrad Med J. 82: 315-322.*
Foster et al. (2011) Am. J. Gastroenterol. 106: 71-77.*
Marimuthu et al. (2013) J. Basic Clin. Physiol. Pharmacol. 24(1): 59-66.*
Chinese medicine treatment of fatty liver wonders, http://www.fuxzy.cn/viewthread.php?tid=8177, Oct. 13, 2009, www.fuxzy.cn, China.
Jiang et al•, "Study on the Optimum Extraction Technoiogyon—the Application of Supercritical Co2 Fluid for Extracting—Macroporous Absorption Resin for Angelica sinensis (Olio.) Diels", Chinese Archives of Traditional Chinese Medicine, Mar. 2008, pp. 569-571, vol. 26, No. 3, Mar. 26, 2008.
Sun et al. (2006) Natural Product Research, vol. 20, No. 9, pp. 835-841.
Kikuzaki et al. (2002) J. Agric. Food Chem. 50, 2161-2168.
Rukkumani et al. (2004) J. Med. Food 7 (4) 456-461.
Nykanen et al. (1991) J. Ess. Oil Res., 3, 229-236.

* cited by examiner

*Primary Examiner* — Chris R Tate
*Assistant Examiner* — Russell Fiebig
(74) *Attorney, Agent, or Firm* — Muncy, Geissler, Olds & Lowe, P.C.

(57) ABSTRACT

In the present invention, a method of inhibiting fatty liver disease is disclosed. The method comprises administrating an effective amount of an extract of *Angelica acutiloba* Kitagawa to a subject in need thereof at a dosage of 150 to 600 mg for per kilogram per day of the subject in need, lasting for 4 weeks. The extract of *Angelica acutiloba* Kitagawa is obtained by extracting roots of *Angelica acutiloba* Kitagawa through a process of supercritical fluid extraction, water extraction, or organic solvent extraction. A preparation method of the extract of *Angelica acutiloba* Kitagawa is also disclosed in the present invention.

4 Claims, 7 Drawing Sheets
(3 of 7 Drawing Sheet(s) Filed in Color)

METHOD OF TREATING FATTY LIVER DISEASE

BACKGROUND OF THE INVENTION

1. Field of the Invention

The present invention relates to an extract of *Angelica acutiloba* Kitagawa for treating fatty liver and, more particularly, to an extract of *Angelica acutiloba* Kitagawa for treating fatty liver disease and a medication comprising the said extract of *Angelica acutiloba* Kitagawa for treating fatty liver.

2. Description of the Related Art

Fatty liver, also known as fatty liver disease (FLD), is characterized by large vacuoles of lipid, such as triglyceride, accumulating in liver cells, or steatosis (also called fatty degeneration) within liver cell.

It is reported that, 25% to 36% of adults in Taiwan suffer from fatty liver disease. However, due to the non-obviousness of fatty liver disease in clinical symptoms, for example non-specific gastrointestinal disorders including upper abdomen pain, loss of anoresia, flatulence, burnout, or liver pain and, thus that people usually aware of their pathogenesis only when acute hepatomegaly and fulminant hepatitis occur or in an abdominal ultrasound diagnosis.

Fatty liver disease is mainly occurred in person who has excessive drinking, obesity, malnutrition, diabetes (having high incidence, about 80%, to fatty liver disease) or use steroid for a long time. Generally, conventional treatments of fatty liver disease depends on what is causing it, and basically, treating the underlying cause will reverse the process of steatosis accompanied with healthy diet and moderate exercises so as to relieve the accumulation of triglyceride in liver cells.

However, negative attitudes in conventional treatment of fatty liver disease usually result in disease progression, such as hypercholesterolemia, poor blood circulation, slow bloodstream and increase incidences to cardiovascular diseases and serious complication, such as chronic hepatitis, fulminant hepatitis, cirrhosis or liver cancer, leading to irreversible consequences.

On the other hand, for people who have hypercholesterolemia and fatty liver, conventional hypolipidemic agents only can effectively reduce level of blood fat, but is poor in reducing fat in liver cells. Also, the conventional hypolipidemic agents will increase hepatotocity after long-term of treatment. Besides, for people who only have fatty liver disease, the conventional hypolipidemic agents are useless in treatment. As a result, due to the inconvenience of the conventional treatments, there is no preferable medication for suppressing fatty liver disease till now.

SUMMARY OF THE INVENTION

The primary objective of this invention is to provide an extract of *Angelica acutiloba* Kitagawa for treating fatty liver disease, which can reduce accumulation of lipid in liver cells and, thus avoid pathogenesis of fatty liver disease.

The secondary objective of this invention is to provide a medication for treating fatty liver disease, which comprises natural herbal extract obtained from *Angelica acutiloba* Kitagawa and will not cause any hepatotoxicity to life-form.

An extract of *Angelica acutiloba* Kitagawa for treating fatty liver disease is obtained by extracting roots of *Angelica acutiloba* Kitagawa through a process of supercritical fluid extraction, water extraction, or organic solvent extraction.

A medication for treating fatty liver disease, comprise an extract of *Angelica acutiloba* Kitagawa obtained as defined in claim 1 or an extract of *Angelica acutiloba* Kitagawa as defined in claim 4; and a pharmaceutical acceptable carrier substrate or excipient.

Further scope of the applicability of the present invention will become apparent from the detailed description given hereinafter. However, it should be understood that the detailed description and specific examples, while indicating preferable embodiments of the invention, are given by way of illustration only, since various others will become apparent from this detailed description to those skilled in the art.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will become more fully understood from the detailed description given herein below and the accompanying drawings which are given by way of illustration only, and thus are not limitative of the present invention, and wherein.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

The present invention relates to an extract of *Angelica acutiloba* Kitagawa, which can significantly reduce levels of total cholesterol, total triglyceride and high-density lipoprotein in blood, and particularly avoid the accumulation of triglyceride and promote the metabolism of fat in liver cells of life-form, so as to reduce the incidence to fatty liver disease.

Figure 1:
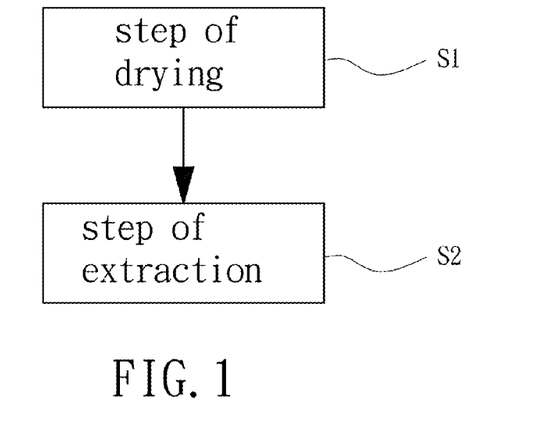
FIG. 1 is a diagram illustrating a preparation method of an extract of *Angelica acutiloba* Kitagawa in the present invention.

In FIG. 1, a preparation method of the extract of *Angelica acutiloba* Kitagawa of the present invention is shown and comprises steps of "drying S1," and "extracting S2," wherein the extract of *Angelica acutiloba* Kitagawa of the present invention is but not limit to be obtained via the preparation method. It is suggested the preparation method can also be processed with a proper modification by a person who has ordinary skill in the art.

In the step of "drying S1," roots of *Angelica acutiloba* Kitagawa is prepared and dried till a water content of the roots of *Angelica acutiloba* Kitagawa decreasing at 10% or less than 10% to obtain a sample of dry *Angelica acutiloba* Kitagawa. Precisely, the roots of *Angelica acutiloba* Kitagawa are but not limit to be dried through a process of lyophilization, spray drying, evaporation or heating drying. In the present invention, the roots of *Angelica acutiloba* Kitagawa is preferably obtained from its main roots, lateral roots, bases or fibers. In a preferable example of the present invention, roots of *Angelica acutiloba* Kitagawa are prepared and dried via a process of lyophilization to obtain a dry herbal sample.

*Angelica acutiloba* Kitagawa, being sweet, spicy and moderate in test, is widely in used in Chinese traditional medicine to treat heart, liver, and spleen related diseases. *Angelica acutiloba* Kitagawa is rich in ferulic acid and ligustilide, which has therapeutic effects of anti-bacterium, anti-oxidization, anti-inflammation, and anti-tumor. In fact, ferulic acid performs well in anti-oxidization and clearance of free radicals, and which can avoid peroxidation of lipid, reduce production of fat in blood, and suppress synthesis of cholesterol in liver cells. With such performance in the step of "drying S1," active substances, such as ferulic acid and ligustilide, is condensed and apt to be easily extracted in the step of "extracting S2" with a high efficiency.

Figure 2:
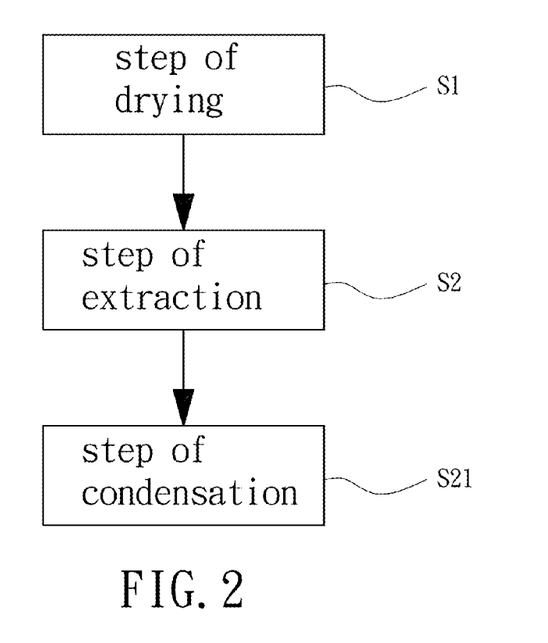
FIG. 2 is a diagram illustrating a preparation method of an extract of *Angelica acutiloba* Kitagawa in the present invention.
Figure 3:
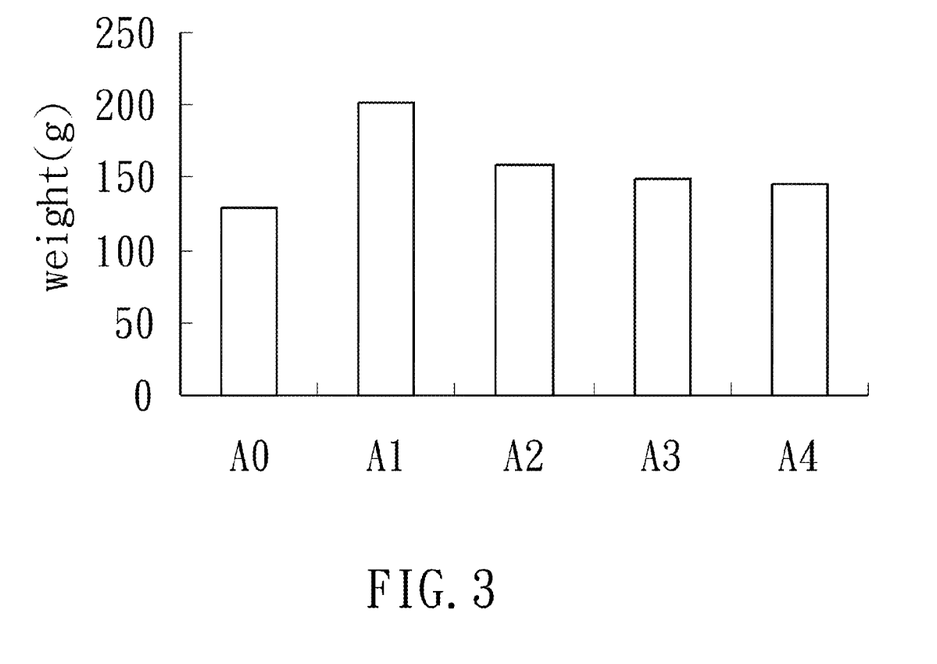
FIG. 3 is a bar chart illustrating body weight of hamsters in Groups A0-A4.
Figure 4:
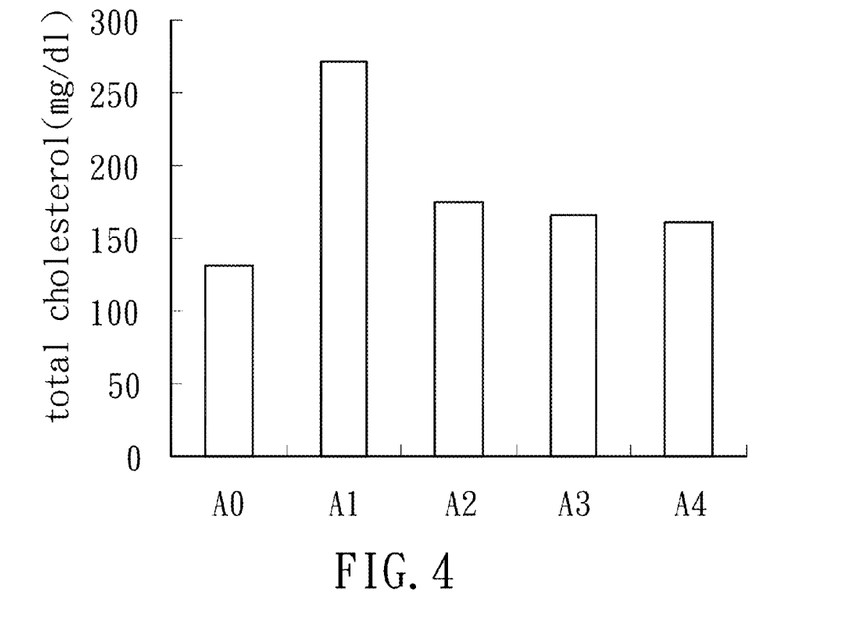
FIG. 4 is a bar chart illustrating levels of total cholesterol in hamsters of Groups A0-A4.
Figure 5:
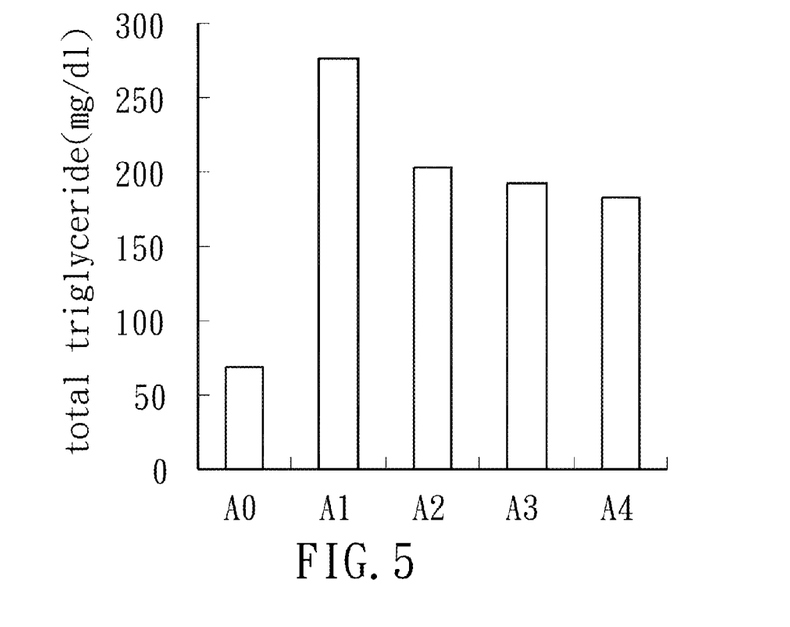
FIG. 5 is a bar chart illustrating levels of total triglyceride in hamsters of Groups A0-A4.
Figure 6:
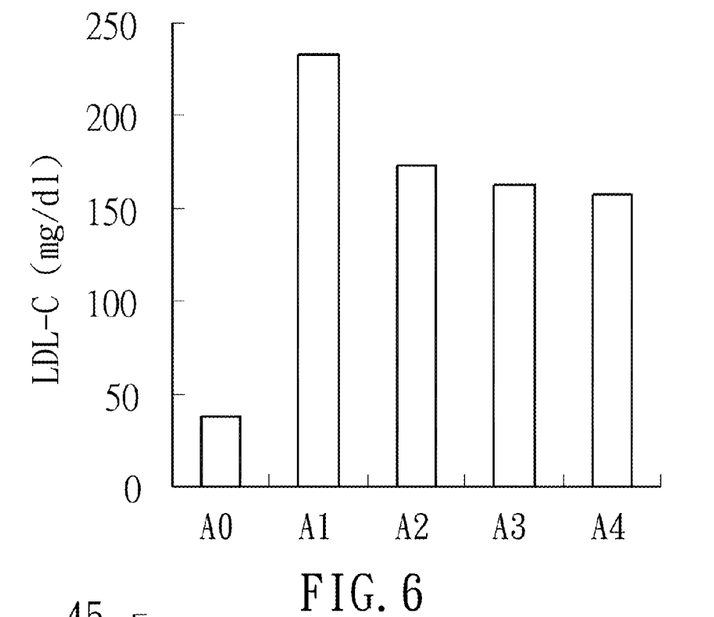
FIG. 6 is a bar chart illustrating levels of low-density lipoprotein in hamsters of Groups A0-A4.
Figure 7:
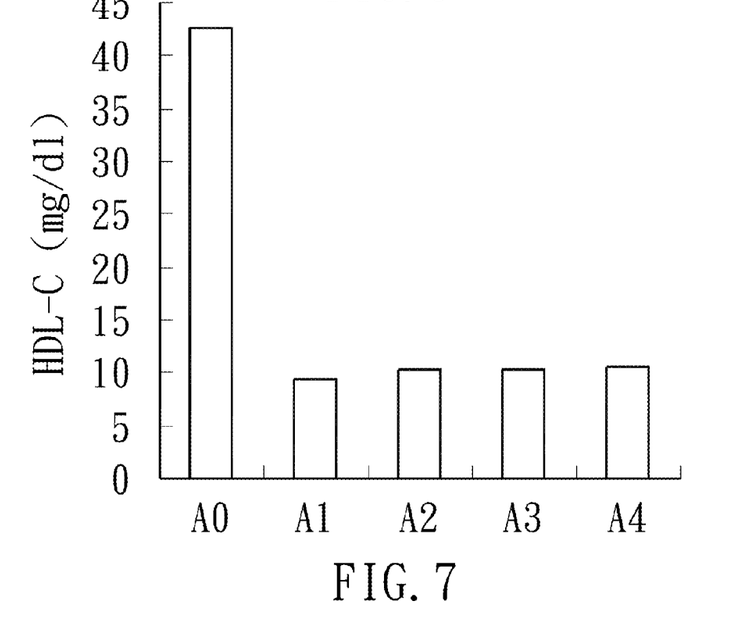
FIG. 7 is a bar chart illustrating levels of high-density lipoprotein in hamsters of Groups A0-A4.
Figure 8:
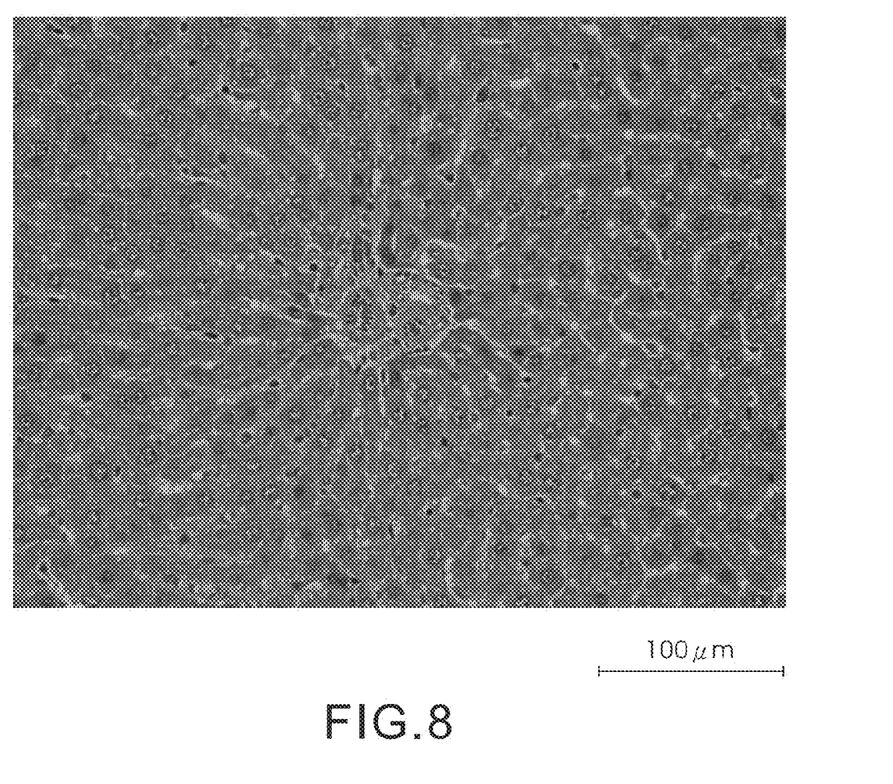
FIG. 8 is a histosection datum of liver tissue in hamsters in Group A0.
Figure 9:
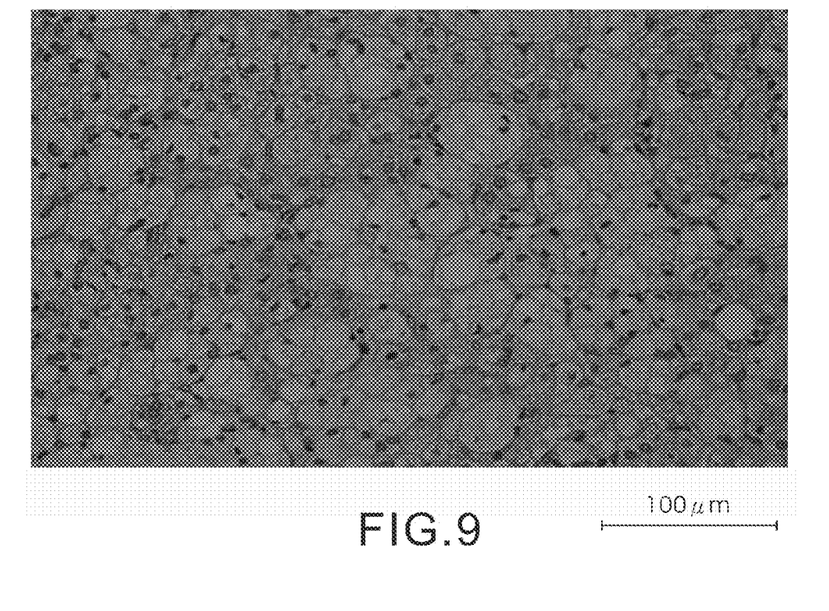
FIG. 9 is a histosection datum of liver tissue in hamsters in Group A1.
Figure 10:
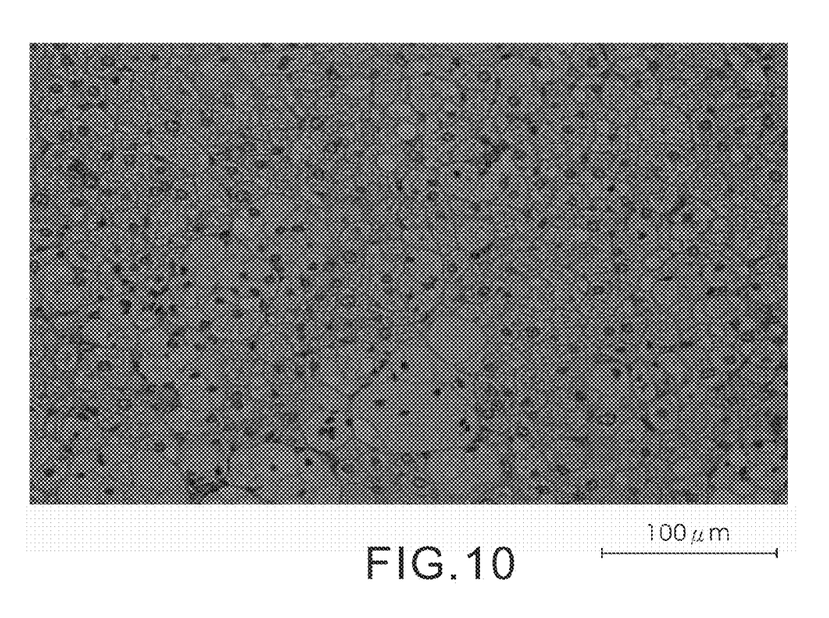
FIG. 10 is a histosection datum of liver tissue in hamsters in Group A2.
Figure 11:
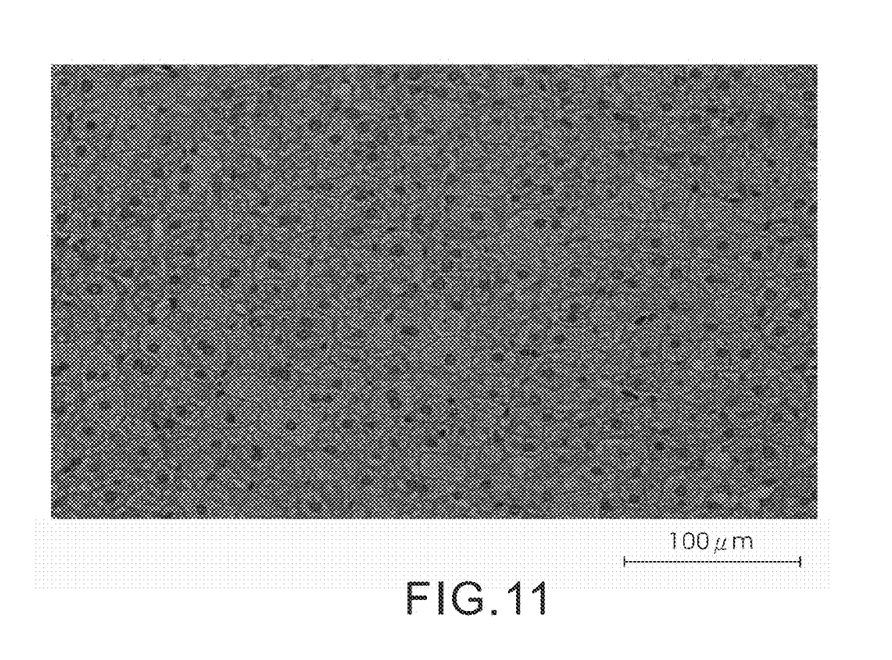
FIG. 11 is a histosection datum of liver tissue in hamsters in Group A3.
Figure 12:
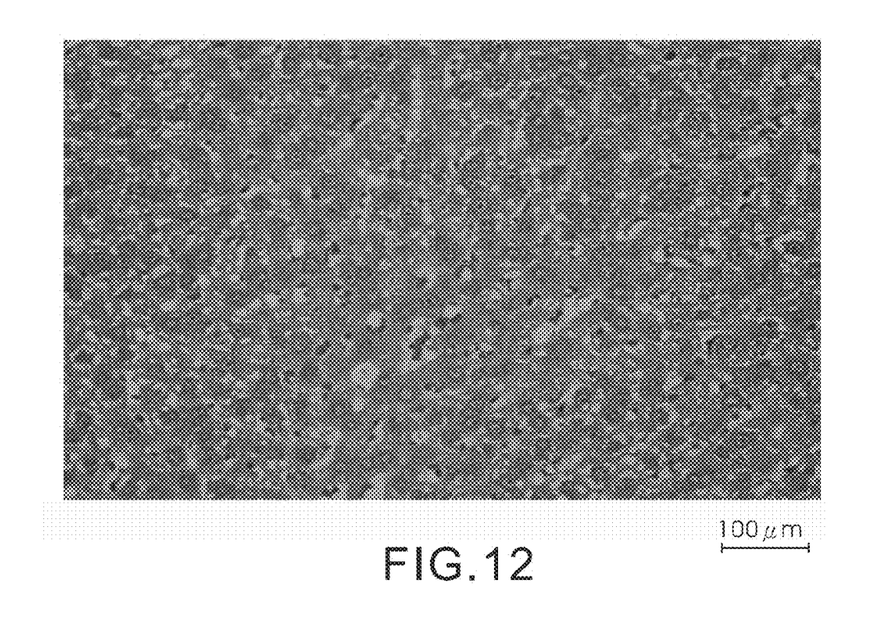
FIG. 12 is a histosection datum of liver tissue in hamsters in Group A4.

In the step of "extracting S2," the sample of dry *Angelica acutiloba* Kitagawa is extracted with a solvent, to obtain an extract of *Angelica acutiloba* Kitagawa. For example, the step of "extracting S2" can be processed through a method of supercritical fluid extraction, water extraction, or organic solvent extraction. Additionally, with reference to FIG. 2, a step of "condensation S21," needs to be further processed if the method of water extraction or organic solvent extraction is performed in the step of "extracting S2," wherein active substances of *Angelica acutiloba* Kitagawa obtained in water or solvent are condensed via a process of lyophilization, spray drying, evaporation or heating drying to obtain the extract of *Angelica acutiloba* Kitagawa. In an embodiment of the present invention, the sample of dry *Angelica acutiloba* Kitagawa is but not limit to be extracted via a 1000 bar extraction pilotplant, with supercritical carbon dioxide fluid extracting the sample of *Angelica acutiloba* Kitagawa at 200-650 bar and 50-65° C. With such performance in the present embodiment, the supercritical carbon dioxide fluid used in the step of "extracting S2" will become vapor after extracting, so as to obtain the extract of *Angelica acutiloba* Kitagawa as dry without additional condensation in the step of "condensation S21." Therefore, the extract of *Angelica acutiloba* Kitagawa obtained from the present embodiment will be easy in use in pharmaceutical industry.

In the next paragraphs, the therapeutic effect of the extract of *Angelica acutiloba* Kitagawa on avoid incidence to fatty liver disease is demonstrated in an animal trial by preparing and feeding hypercholesterolemia animal with the extract of *Angelica acutiloba* Kitagawa, and valuating the course of fatty liver disease via analyzing levels of total cholesterol (TC), total triglyceride (TG), low-density lipoprotein (LDL-C), high-density lipoprotein (HDL-C) and liver distosection thereof.

In the present embodiment, male and 4-weeks-old Golden Syrian hamsters purchased from National Laboratory Animal Center in Taiwan are prepared and housed at a standard laboratory environment, such as keeping 25±1° C. and with a 12 hours light/dark cycle, wherein the hamster's bodies weight and or diet weight are monitored and recorded during the housing period.

In TABLEs 1 and 2, male and 4-weeks-old Golden Syrian hamsters are divided into 5 groups (8 hamsters in each group), including a group of (A0), as a control and fed with chow diet comprising of 18% protein, 10% moisture, 6% crude fat, 6% crude fiber, 6% ash, and 54% soluble nitrogen free extract during housing, and groups of (A1) to (A4) all fed with high-fat diet comprising TestDiet 5TJT with 1% cholesterol during housing, with their body weight and levels of TC, TG, LDL-C and HDL-C being recorded during 4 weeks of housing. With such arrangement, hyperlipidemic hamsters (HL hamster) are successfully obtained after 4 weeks of housing (8-weeks-old hamster), having a TC level high than 200 mg/dl, a TG level high than 150 mg/dl, a LDL-C level higher than 130 mg/dl, and a HDL-C level lower than 40 mg/dl.

TABLE 1

Weights and Levels of Blood Lipid of Hamsters in Groups (A0) to (A4) before Housing (4-Weeks-Old Hamster)

| Groups | Weight (g) | TG(mg/dl) | TG(mg/dl) | LDL-C(mg/dl) | HDL-C(mg/dl) |
|---|---|---|---|---|---|
| A0 | 108.2 ± 1.2 | 127.2 ± 2.1 | 61.2 ± 2.1 | 32.1 ± 1.3 | 45.4 ± 1.0 |
| A1 | 142.3 ± 2.0 | 223.5 ± 2.6 | 211.5 ± 2.6 | 201.4 ± 1.8 | 10.2 ± 0.9 |
| A2 | 148.2 ± 1.7 | 219.6 ± 1.5 | 204.9 ± 2.1 | 204.9 ± 2.1 | 10.6 ± 1.2 |
| A3 | 140.5 ± 2.1 | 202.4 ± 1.8 | 197.2 ± 1.9 | 190.5 ± 2.4 | 10.8 ± 0.7 |
| A4 | 138.3 ± 1.8 | 191.5 ± 1.4 | 193.6 ± 1.7 | 181.3 ± 1.8 | 10.7 ± 0.4 |

TABLE 2

Weights and Levels of Blood Lipid of Hamsters in Groups (A0) to (A4) after Housing (8-Weeks-Old Hamster)

| Groups | Weight(g) | TG (mg/dl) >200 mg/dl | TG (mg/dl) >150 mg/dl | LDL-C (mg/dl) >130 mg/dl | HDL-C (mg/dl) <40 mg/dl |
|---|---|---|---|---|---|
| A0 | 118.6 ± 1.6 | 129.5 ± 1.9 | 65.4 ± 2.0 | 36.4 ± 1.7 | 43.2 ± 1.2 |
| A1 | 186.4 ± 2.1 | 252.1 ± 2.3 | 250.8 ± 2.3 | 228.1 ± 2.0 | 10.3 ± 0.7 |

TABLE 2-continued

Weights and Levels of Blood Lipid of Hamsters in Groups
(A0) to (A4) after Housing (8-Weeks-Old Hamster)

| Groups | Weight(g) — | TG (mg/dl) >200 mg/dl | TG (mg/dl) >150 mg/dl | LDL-C (mg/dl) >130 mg/dl | HDL-C (mg/dl) <40 mg/dl |
|---|---|---|---|---|---|
| A2 | 148.1 ± 1.9 | 186.3 ± 1.7 | 209.2 ± 2.0 | 187.4 ± 1.9 | 10.4 ± 1.0 |
| A3 | 139.3 ± 2.0 | 174.2 ± 1.5 | 195.2 ± 1.7 | 170.8 ± 2.1 | 10.9 ± 0.8 |
| A4 | 134.3 ± 1.7 | 168.3 ± 1.9 | 189.1 ± 1.9 | 164.3 ± 1.9 | 10.9 ± 0.6 |

In the following 4 weeks, the hamsters in group (A0) are continually fed with chow diet and water, but the HL hamsters in groups (A1) to (A4) are fed with high-fat diet and the extract of *Angelica acutiloba* Kitagawa in various dosages, such as 150, 300 and 600 mg per kg of hamster everyday with reference to TABLE 3. Furthermore, levels of TC, TG, LDL-C and HDL-1 of hamsters (12-weeks-old) in each group are further monitored and recorded in TABLE 3 in the present embodiment.

TABLE 3

Feeding and Levels of Blood Lipid of Hamsters in Groups (A0)
to (A4) after 4 Weeks of Housing (12-Weeks-Old Hamster)

| Groups | Feeding | (mg/kg/day) | Weight (g) | TC (mg/dl) | TG (mg/dl) | LDL-C (mg/dl) | HDL-C (mg/dl) |
|---|---|---|---|---|---|---|---|
| A0 | Chow diet | 1 ml water | 129.3 ± 1.9 | 131.3 ± 2.1 | 68.2 ± 1.7 | 38.2 ± 1.9 | 42.7 ± 1.5 |
| A1 | High-fat | 1 ml water | 201.2 ± 2.3 | 271.3 ± 2.6 | 276.2 ± 3.6 | 233.1 ± 2.3 | 9.3 ± 1.3 |
| A2 | diet | 150 extract of *Angelica acutiloba* Kitagawa | 158.2 ± 3.4 | 175.2 ± 1.8 | 203.1 ± 3.4 | 173.2 ± 2.8 | 10.4 ± 1.2 |
| A3 | | 300 | 148.4 ± 2.7 | 166.2 ± 2.3 | 192.4 ± 2.6 | 162.4 ± 3.0 | 10.2 ± 1.2 |
| A4 | | 600 | 145.0 ± 3.1 | 160.5 ± 2.0 | 182.3 ± 2.8 | 157.2 ± 3.1 | 10.5 ± 1.0 |

With reference to TABLE 3 and FIGS. 3 to 7, the hamsters of group (A0) show normal weight and levels of blood lipid after feeding water or the extract of *Angelica acutiloba* Kitagawa. Yet, in comparison with hamsters in group (A1), either body weight or levels of blood lipid of hamsters in group (A2) to (A4) are significantly lower, with their body weight having 40-55 grams lower than that of hamsters in group (A1) (see FIG. 3), with their levels of TC having 95-110 mg/dl lower than that of hamsters in group (A1) (see FIG. 4), with their levels of TG having 70-95 mg/dl lower than that of hamsters in group (A1) (see FIG. 5), with their levels of HDL-C and HDL-C having 60-76 mg/dl lower than that of hamsters in group (A1) (see FIG. 7), but with their levels of LDL-C having 0.9-1.2 mg/dl higher than that of hamsters in group (A1) (see FIG. 6). It is verified that hamsters in groups (A2) to (A4) and groups (A1) show dramatic difference in body weight, and levels of TC, TG and HDL-C.

It is suggested that with the treatment of the extract of *Angelica acutiloba* Kitagawa in the present invention, it is sufficient to suppress hypercholesterolemia by moderating levels of blood lipid, particularly for levels of TC and TG in life-forms.

For further proving pathogenesis of fatty liver in hypercholesterolemia animal and the therapeutic effects of the extract of *Angelica acutiloba* Kitagawa in treating of fatty liver disease, gamsters, hamsters (12-weeks-old) in each group are dissected, and histosection data of each group are prepared, analyzing pathogenic affection in liver tissue of each hamster, including hepatocellular hydropic degeneration, central lobular necrosis, hepatic lipidosis, and hepatic fibrosis. Precisely, the histosection data of liver tissues in each hamsters are collected from the same site at right lobe of liver tissue, being 1 cm2 of area, followed by fixed with 10% neutral formalin solution, embodied in paraffin, and stained by hematoxylin and eosin stain (HE stain). In the present invention, the degrees of pathogenic affection, including hepatocellular hydropic degeneration, central lobular necrosis, hepatic lipidosis, and hepatic fibrosis of liver tissue, in each hamster are presented as score and summarized in TABLE 4.

In FIGS. 8 to 12, it is noted that vacuoles within liver tissues are lipid, as more vacuoles placing in liver tissue as more serious it does in accumulation of lipid in liver. Wherein, rations of vacuoles in liver tissue are 84%, 64%, 52%, and 40% respectively in hamsters of groups (A1), (A2), (A3) and (A4). It is clear that the rations of vacuoles in liver tissue in hamsters of groups (A2) to (A4) are significantly lower than that of hamsters of groups (A1) (p<0.05). Furthermore, there is no dramatic difference in rations of vacuoles in liver tissue between hamsters of groups (A4) and (A0). Hence, it is proved that the extract of *Angelica acutiloba* Kitagawa of the present invention can relieve the accumulation of lipid in liver tissue of hypercholesterolemia animal.

It is noted that the hydropic degeneration is characterized by a large amount of bubble or limpid liquid in cytoplasm caused by abnormal metabolism in liver cells, wherein the symptoms of hydropic degeneration is reversible if causes thereof has removed.

It is noted that the central lobular necrosis is characterized by irreversible necrosis around the central vein leading to condensation of nucleus and cytoplasm.

It is noted that the hepatic fibrosis is characterized by a large amount of cell necrosis occurred at central vein developing into excessive connective tissue in the liver, which is an irreversible symptom.

In the present invention, the pathogenic affections in each group is reviewed and quantified by a doctor in pathology department without knowing detail procedure of the trial of the present invention, wherein, point "0" means no symptom is occurred, point "1" means 25% and less than 25% of area in histosection has symptom, point "2" means 25~50% of area in histosection has symptom, point "3" means 50~75% of area in histosection has symptom, point "4" means 75% and more than 75% of area in histosection has symptom.

TABLE 4

Pathogenic Affection in Liver Tissue of Hamsters in Groups (A0) to (A4) after 4 Weeks of Housing (12-Weeks-Old Hamster)

| Groups | Weight of liver tissue (g) | Hydropic degeneration | Central lobular necrosis | Hepatic lipidosis | Hepatic fibrosis |
|---|---|---|---|---|---|
| A0 | 3.78 ± 1.23 | 0.0 ± 0.0 | 0.0 ± 0.0 | 0.0 ± 0.0 | 0.0 ± 0.0 |
| A1 | 10.22 ± 1.29 | 4.5 ± 0.1 | 3.5 ± 0.3 | 4.2 ± 0.3 | 4.2 ± 0.3 |
| A2 | 8.38 ± 1.22 | 3.3 ± 0.1 | 2.9 ± 0.2 | 3.1 ± 0.2 | 3.2 ± 0.2 |
| A3 | 7.54 ± 1.12 | 3.2 ± 0.2 | 2.8 ± 0.1 | 2.9 ± 0.2 | 2.6 ± 0.2 |
| A4 | 6.83 ± 1.23 | 2.3 ± 0.1 | 2.5 ± 0.1 | 2.8 ± 0.3 | 2.0 ± 0.1 |

With reference to TABLE 4, it is obvious that the histosection datum of group (A1) has the most serious pathogenic affection among other groups ($p<0.05$). On the other hand, the histosection datum of group (A4) has the least serious pathogenic affection among other groups. It is suggested that, the extract of *Angelica acutiloba* Kitagawa of the present invention, preferably at a dosage of 150~600 mg for per kg of individual per day, can effectively relieve symptoms of fatty liver in hypercholesterolemia animal and prevent from fatty liver disease.

It seems that with treatment of the extract of *Angelica acutiloba* Kitagawa in the present invention, the levels of total cholesterol, total triglyceride, and high-density lipoprotein in hypercholesterolemia animal can be significantly controlled, so as to protect liver and prevent from fatty liver disease.

In summary, through the present invention, an *angelica* extract of *Angelica acutiloba* Kitagawa for treating fatty liver is provided, which can reduce accumulation of lipid in liver cells and, thus avoid pathogenesis of fatty liver disease, with the levels of total cholesterol, total triglyceride, and high-density lipoprotein in hypercholesterolemia animal being successfully controlled by feeding them the *angelica* extract of *Angelica acutiloba* Kitagawa of the present invention. Hence, it is believed that the *angelica* extract of *Angelica acutiloba* Kitagawa can effectively protect liver tissues, and reduce incidences to fatty liver disease.

In the present invention, the extract of *Angelica acutiloba* Kitagawa is rich in ferulic acid and ligustilide, which can avoid peroxidation of lipid, reduce levels of total cholesterol, total triglyceride, and high-density lipoprotein in liver, so as to prevent from fatty liver disease. Therefore, with the extract of *Angelica acutiloba* Kitagawa of the present invention, a medication comprising the extract of *Angelica acutiloba* Kitagawa is also easily obtained, and which comprises natural herbal extract obtained from *Angelica acutiloba* Kitagawa and shares natural therapeutic properties to fatty liver, being easy to put to used in pharmaceutical industries. Furthermore, the medication comprising the extract of *Angelica acutiloba* Kitagawa of the present invention can be manufactured into any form of medicament including a pill, pastil, powder, capsule or solution, even in combination with other food products or drinks. In general, the medication of the present invention can be given individually or combined with any pharmaceutical acceptable carrier substrate or excipient, preferably in a dosage of 150 to 600 mg for per kg of weight and lasting for 4 weeks, so as to effectively control the pathogenesis of fatty liver in life-forms. In this way, the treatments for fatty liver disease will become easier and more acceptable to general public since no hepatotoxicity involved in the medication of the present invention.

Thus, since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A method of treating fatty liver disease, comprising administrating an effective amount of an extract of *Angelica acutiloba* Kitagawa to a subject in need thereof, wherein the extract of *Angelica acutiloba* Kitagawa is administered for 4 weeks at a dosage of 150 to 600 mg/kg bodyweight/day;
   wherein the extract of *Angelica acutiloba* Kitagawa is obtained by extracting roots of *Angelica acutiloba* Kitagawa supercritical carbon dioxide fluid extraction.

2. The method of treating fatty liver disease as defined in claim 1, wherein the extract of *Angelica acutiloba* Kitagawa is orally administrated to the subject.

3. The method of treating fatty liver disease as defined in claim 1, wherein the roots of *Angelica acutiloba* Kitagawa comprises main roots, lateral roots, bases or fibers.

4. The method of treating fatty liver disease as defined in claim 1, wherein the supercritical carbon dioxide fluid extraction is performed at 200 to 650 bar and 50 to 65° C.

* * * * *